United States Patent [19]

Bright

[11] 4,166,901

[45] Sep. 4, 1979

[54] 4″-DEOXY-4″-ARYLGLYOXAMIDO- AND AROYLTHIOFORMAMIDO DERIVATIVES OF OLEANDOMYCIN AND ITS ESTERS

[75] Inventor: Gene M. Bright, Groton, Conn.

[73] Assignee: Pfizer Inc., New York, N.Y.

[21] Appl. No.: 952,411

[22] Filed: Oct. 23, 1978

Related U.S. Application Data

[63] Continuation-in-part of Ser. No. 866,890, Jan. 3, 1978, abandoned.

[51] Int. Cl.$^2$ .............................. C07H 17/08
[52] U.S. Cl. .................... 536/9; 536/17 R; 424/180
[58] Field of Search ............................ 536/9

[56] References Cited

U.S. PATENT DOCUMENTS

| | | | |
|---|---|---|---|
| 4,085,119 | 4/1978 | Myers | 536/9 |
| 4,090,017 | 5/1978 | Sciavolino | 536/9 |
| 4,098,993 | 7/1978 | Bright | 536/9 |

Primary Examiner—Johnnie R. Brown
Assistant Examiner—Blondel Hazel
Attorney, Agent, or Firm—Francis X. Murphy; Charles J. Knuth; Albert E. Frost

[57] ABSTRACT

Derivatives of oleandomycin, its 11-monoalkanoyl, 2-monoalkanoyl and 11,2′-dialkanoyl esters having at the 4″-position an amino group substituted with —C(=O)—C(=O)—R$_3$ or —C(=S)—C(=O)—R$_3$ wherein R$_3$ is alkyl having from one to four carbon atoms, phenyl, substituted phenyl, or a heterocyclyl group, their preparation and use as antibacterial agents is described.

32 Claims, No Drawings

4''-DEOXY-4''-ARYLGLYOXAMIDO- AND AROYLTHIOFORMAMIDO DERIVATIVES OF OLEANDOMYCIN AND ITS ESTERS

CROSS-REFERENCE TO RELATED APPLICATIONS

This application is a continuation-in-part of copending application Ser. No. 866,890 filed Jan. 3, 1978 now abandoned.

BACKGROUND OF THE INVENTION

1. Field of the Invention

This invention relates to a structurally unique group of macrolides and, more particularly, to derivatives of oleandomycin, its 11-mono-, 2'-mono- and 11,2'-dialkanoyl esters having at the 4''-position an amino group substituted with —C(=O)—C(=O)—$R_3$ or —C(=S)—C(=O)—$R_3$ wherein $R_3$ is phenyl, substituted phenyl, or a heterocyclic group, and to methods for their preparation. The compounds are antibacterial agents.

2. Description of the Prior Art

Oleandomycin, a macrolide antibiotic produced by fermentation, was first described in U.S. Pat. No. 2,757,123. It has the formula, the absolute configuration of which is shown below:

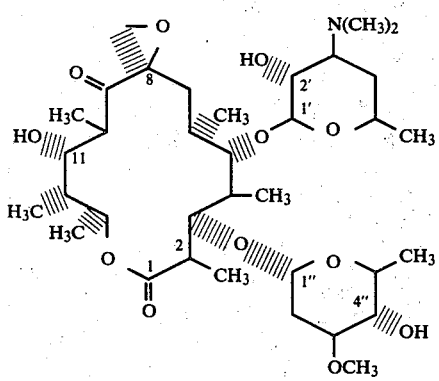

It consists of three main structural features: the L-oleandrose moiety, the desosamine moiety and the oleandolide moiety.

Derivatization of oleandomycin has focused primarily upon the formation of esters at one or more of three hydroxy groups located at the 2', 4'' and 11-positions. Mono- di and triacyl esters wherein the acyl moiety is derived from a lower aliphatic hydrocarbon monocarboxylic acid having from two to six carbon atoms are described in U.S. Pat. No. 3,022,219.

Aminohydrin derivatives of oleandomycin are reported by Kastrons et al., *Khim. Geterosikl Soedin* (2), 168–71 (1974); C.A. 80, 145986n (1974). The compounds, for which no utility is reported, are prepared by treating oleandomycin with a dialkylamine or a heterocyclic amine in a sealed tube for twenty hours at 30° C. The epoxide moiety at the 8-position is the site of reaction.

SUMMARY OF THE INVENTION

There has now been found a series of oleandomycin derivatives each of which exhibits valuable antibacterial activity in vitro and many of which exhibit in vivo activity by the parenteral and oral routes of administration, particularly against Gram-positive microorganisms. The compounds of this invention have formula II below wherein the wavy line connecting the substituted amino group at the 4''-position in generic to and embracive of both epimeric forms:

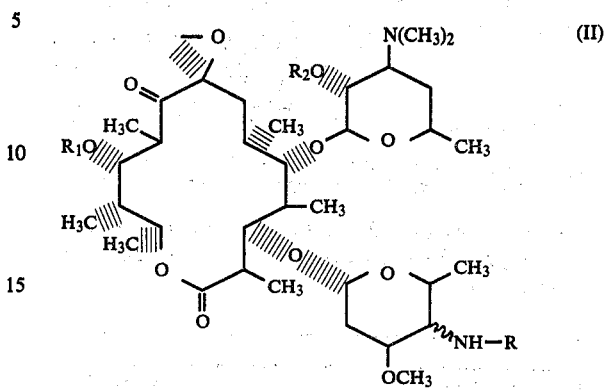

wherein R is selected from the group consisting of

 (a)

and

 (b)

wherein $R_3$ is selected from the group consisting of a first subgroup consisting of

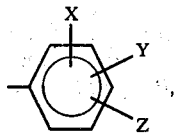, a second subgroup consisting of
  heterocyclyl, and
a third subgroup consisting of
  alkyl having from one to four carbon atoms;
wherein each of X and Y is selected from the group consisting of hydrogen, chloro, bromo, fluoro, alkyl having from one to four carbon atoms and alkoxy having from one to four carbon atoms; and Z is selected from the group consisting of X, dimethylamino, nitro and amino;

heterocyclyl is selected from the group consisting of thienyl, furyl and pyridyl;

and each of $R_1$ and $R_2$ is selected from the group consisting of hydrogen and alkanoyl having from two to three carbon atoms.

Also included in the present invention are the pharmaceutically acceptable acid addition salts of compounds of formula II above. Representative of such salts, but not limited thereto, are the hydrochloride, hydrobromide, phosphate, sulfate, formate, acetate, propionate, butyrate, citrate, glycolate, lactate, tartrate, malate, maleate, fumarate, gluconate, stearate, mandelate, pamoate, benzoate, succinate, lactate, p-toluenesulfonate and aspartate.

Favored because of their greater biological activity relative to that of other compounds described herein are compounds of formula II wherein $R_1$ is alkanoyl or hydrogen, $R_2$ is hydrogen, and R has the values shown below:

| R | R₃ | | X | Y | Z |
|---|---|---|---|---|---|
| —C(=O)—C(=O)—R₃ | 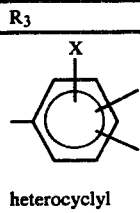 | | X | H | H | Z |
| —C(=S)—C(=O)—R₃ | | | | Y | H | Cl | alkoxy |
| —C(=S)—C(=O)—R₃ | heterocyclyl | | | | | |
| —C(=O)—C(=O)—R₃ | | | | | | |

Preferred compounds are those wherein R₁ is acetyl or hydrogen; R₂ is hydrogen and R has the values shown below:

| R | R₃ | X | Y | Z |
|---|---|---|---|---|
| —C(=O)—C(=O)—R₃ | 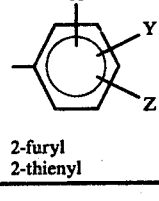 | H | H | H |
| —C(=S)—C(=O)—R₃ | | | | |
| —C(=S)—C(=O)—R₃ | 2-furyl | | | |
| —C(=O)—C(=O)—R₃ | 2-thienyl | | | |

Compounds of formula II, including the epimeric forms thereof, and their pharmaceutically acceptable salts are effective antibacterial agents against Gram-positive microorganisms, e.g. *Staphylococcus aureus* and *Streptococcus pyogenes*, in vitro and many are active in vivo via the parenteral and oral routes of administration. Many of the compounds (and their salts) are also active against certain Gram-negative microorganisms, such as cocci, e.g. *Pasteurella multocida* and *Neisseria sicca*.

DETAILED DESCRIPTION OF THE INVENTION

The structurally unique oleandomycin derivatives of this invention of formula II are prepared by acylation of an amine of formula III:

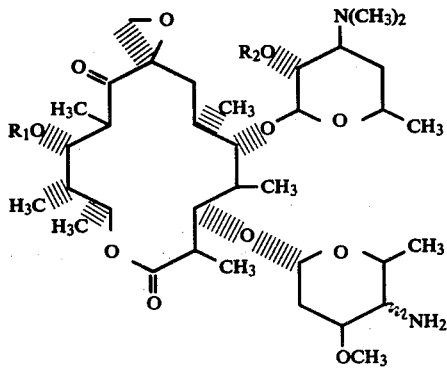

wherein each of R₁ and R₂ is as previously defined, with appropriate acylating agents which afford the acyl moieties R₃—C(=O)—C(=O)— or R₃—C(=O)—C(=S)—. Suitable as acylating agents are mixed anhydrides, acid azides, carboxylic acids with carbodiimides or alkoxyacetylenes or with other reagents capable of achieving dehydrative coupling, "activated esters" such as thiol esters and phenolic esters, and acid halides. When the acyl moiety is of the formula R₃—C-(—O)—C(=O)—, the preferred acylating agent is the carboxylic acid in the presence of a dehydrative coupling agent such as a carbodiimide, an alkoxyacetylene, N,N′-carbonyldiimidazole, N,N′-carbonyl-s-triazine, N-hydroxyphthalimide, N-hydroxysuccinimide and others known to those skilled in the art. Favored as coupling agents are the carbodiimides, many of which are readily available. Dicyclohexylcarbodiimide is a preferred coupling agent since a by-product of the reaction, dicyclohexylurea, is insoluble in a variety of solvents such as dioxane, tetrahydrofuran, chloroform, and diethyl ether and is readily removed from the reaction mixture, thus simplifying recovery and isolation of the desired product.

Similarly, the use of ethylcarbodiimidomethylated polystyrene (Synthesis, No. 3, 208 [Abstract No. 4682] 1976) as coupling agent affords a convenient route to the desired acyl derivatives since no by-product acylurea is produced to complicate recovery of the desired acyl derivative.

Also favored as coupling agents are various aliphatic carbodiimides bearing tertiary or quaternary amine substituents which render the corresponding by-product urea derivatives soluble in dilute acid or water and facilitate separation of the desired reaction product. Representative of such aliphatic carbodiimides are 1-cyclohexyl-3-(4-diethylaminocyclohexyl)carbodiimide, 1,3-di-(4-diethylaminocyclohexyl)carbodiimide, 1-cyclohexyl-3-(β-diethylaminoethyl)carbodiimide, 1-cyclohexyl-3-(2-morpholinyl-(4)-ethyl)carbodiimide and the corresponding metho p-toluenesulfonate.

The reaction is conducted in a reaction-inert solvent. When using an aliphatic carbodiimide bearing tertiary or quaternary amine substituents, dilute acid or water is generally used as solvent. Pure water can be used as solvent or, alternatively, a mixture of water and a water-miscible solvent can be used. In such instances, the water serves as co-solvent. Acetonitrile is a useful solvent when the coupling agent is an aliphatic carbodiimide having a quaternary amine substituent. When the coupling agent is a carbodiimide other than an aliphatic carbodiimide having tertiary or quaternary amine substituents, an organic solvent is required. Suitable solvents for such coupling agents are diethyl ether, benzene, dioxane, tetrahydrofuran, chloroform and methylene chloride. Alcohols can also be used as solvent but are less desirable because of side reactions with the carbodiimides.

The dehydrative coupling reactions are conducted, in general, under mild conditions; for example, at temperatures ranging from about 20° C. to about 50° C. The molar proportion of dehydrative coupling agent to acylating agent to amine of formula III ranges from about 1:1:1 to about 1:1:1.5.

When the acyl moiety has the formula R₃—C(-=O)—C(=S)—, the favored acylating agent is the acid chloride having the formula R₃—C(=O)—C(=S)—Cl because of the relative availability of such agents. A favored procedure comprises conducting the reaction in a reaction-inert solvent in the presence of an acid acceptor. An excess of the amine reactant of formula III can be used as the acid acceptor. Alternatively, a tertiary alkylamine, such as a trialkylamine having from 3 to 12 carbon atoms, and preferably triethylamine, or other commonly used tertiary organic bases such as pyridine, N,N-dimethylaniline or N-methylmorpholine, can be used as the acid acceptor. The reaction is generally conducted in an inert atmosphere to avoid possible effects of atmospheric oxygen on the reactants. Alternatively, acylation of a compound of formula III with an acid halide is conducted under Schotten-Baumann conditions well known to those skilled in the art.

The molar ratio of the acylthioformyl chloride reactant to amine reactant of formula III can vary widely, e.g. from about 1:1 to about 1:10. Molar ratios of less than 1:1 are avoided for economic reasons to insure maximum reaction of the amine reactant, normally the least readily available of the reactants. Ratios of greater than 1:10 are seldom used since they do not appear to improve the yield of final product. The use of an acid acceptor other than the amine reactant of formula III itself affords satisfactory yields of product with the use of from about 1:1 to about 1:3 moles of amine reactant to the acylating agent. The reaction is essentially an acylation reaction.

Suitable reaction-inert solvents (i.e., those which do not react to any appreciable extent with the reactants or products) are the dimethyl ether of ethylene glycol, tetrahydrofuran, n-dibutylether, diethylether, toluene, acetonitrile and methylene chloride. The principle criteria for the solvent are that it remain liquid at the relatively low temperatures at which the reaction is conducted and, of course, that it solubilize the reactants to an appreciable extent, if not completely.

The reaction is carried out at temperatures from about $-30°$ C. to about 50° C. This temperature range affords a satisfactory rate of reaction and eliminates or minimizes side reactions.

Compounds of formula II wherein $R_3$ is an amino substituted phenyl group are conveniently prepared by reduction of a corresponding compound wherein $R_3$ is a nitro substituted phenyl group. The reduction is readily accomplished by catalytic hydrogenation over a noble metal catalyst such as palladium, especially palladium-on-carbon, in a reaction-inert solvent at ambient temperature.

The required glyoxylic acid reactants having formula $R_3$—C(=O)—C(=O)—OH are known compounds or, when not known, are readily obtainable by methods known to those skilled in the art. Representative procedures for producing glyoxylic acid or α-ketoacids having the above formula are discussed by Waters, in *Chemical Reviews*, 41, 585–598 (1947).

The necessary acylthioformyl chloride reactants having formula $R_3$—C(=O)—C(=S)—Cl are prepared according to the procedure described by Oka et al. in *Tetrahedron Letters*, 2783–2786 (1976), which comprises the reaction of an appropriate ketone having the formula $R_3$—C(=O)—CH$_3$ with 10–15 molar equivalents of thionyl chloride in the presence of 0.02 molar equivalent of pyridine at the reflux temperature.

Where the starting amine of formula III is a mixture of epimers, the above-described acylation reactions produce a mixture of epimers (represented by a wavy line in formula II compounds) which can be separated, if desired. Column chromatography of a chloroform solution of the crude product on silica gel and elution with appropriate solvents, e.g. chloroform-3% methanol, offers a convenient method for separating the epimers. In the present description and illustrations, it is understood that although the compounds are listed as 4″-substituted amino derivatives, both epimers and mixtures thereof are included. Of course, if one begins with a given $C_4″$ epimer of formula III, the corresponding $C_4″$-substituted compound of formula II is produced on acylation.

Diester compounds of formula II; i.e., each of $R_1$ and $R_2$ is alkanoyl, can also be prepared by acylation of the corresponding 11-monoalkanoyl ($R_1$=alkanoyl; $R_2$=H) compound by standard procedures known to those skilled in the art, and as exemplified herein. In this manner, preparation of diester compounds wherein the ester groups differ is readily achieved.

Acid addition salts of the compounds of this invention are readily prepared by treating formula II compounds with at least an equimolar amount of the appropriate acid in a reaction-inert solvent for the formula II compound. When more than one basic group is present in a compound of formula II, the addition of sufficient acid to satisfy each basic group permits formation of poly acid addition salts. The acid addition salts are recovered by filtration if they are insoluble in the reaction-inert solvent, by precipitation by addition of a non-solvent for said salt, or by evaporation of the solvent.

The 11-mono-alkanoyl-, 2′-monoalkanoyl- and 11,2′-dialkanoyl-4″-deoxo-4″-amino-oleandomycin reactants (formula III) are prepared by reductive amination of the corresponding 11-mono-alkanoyl-, 2′-monoalkanoyl- and 11,2′-dialkanoyl-4″-deoxo-4″-oxo-oleandomycins using palladium-on-charcoal, hydrogen (from about 1 to about 500 p.s.i.) and ammonium acetate in a suitable solvent (CH$_3$OH, i-C$_3$H$_7$OH). Alternatively, sodium cyanoborohydride can be used as reducing agent in place of palladium-on-charcoal and hydrogen. The de-esterified derivative is conveniently prepared by solvolysis of the corresponding 2′-monoalkanoyl-4″-deoxo-4″-amino-oleandomycins.

The stereochemistry of the starting materials leading to the antibacterial agents of the present invention is that of the natural material. Oxidation of the 4″-hydroxy groups of oleandomycin, erythromycins A and B, erythromycin A 11,12-carbonate, 6,9-hemiketal ester to a ketone and subsequent conversion of said ketone to the 4″-amines presents opportunity for the stereochemistry of the 4″-substituent to change from that of the natural product. Accordingly, when the 4″-oxo reactants are converted to amines, it is possible that epimeric amines are produced. In actual practice, it is observed that both epimeric amines are present in the final product in varying ratios depending upon the choice of synthetic method. If the isolated product consists predominantly of one of the epimers, said epimer can be purified by such methods as repeated crystallization from a suitable solvent to a constant melting point. The other epimer, the one present in smaller amount in the originally-isolated material, is the predominant product in the mother liquor. It can be recovered therefrom by methods known to those skilled in the art, such as, for example, by evaporation of the mother liquor and repeated recrystallization of the residue to a product of constant melting point or by chromatography. Although the mixture of epimeric amines can be separated by methods known to those skilled in the art, for practical reasons it is frequently advantageous to use said mixture as it is isolated from the reaction. Use of the epimeric mixture of 4″-amino reactants produces, of course, an epimeric mixture of the acylated products. The epimeric mixture thus produced can be separated by methods known to those skilled in the art. However, both epimers of a given compound exhibit the same type of activity and their separation, while desirable, is not always necessary.

The novel oleandomycin derivatives described herein exhibit in vitro activity against a variety of Gram-positive microorganisms and against certain Gram-negative microorganisms such as those of spherical or ellipsoidal shape (cocci). Their activity is readily demonstrated by in vitro tests against various microorganisms in a brain-heart infusion medium by the usual two-fold serial dilution technique. Their in vitro activity renders them useful for topical application in the form of ointments, creams and the like; for sterilization purposes, e.g. sickroom utensils; and as industrial antimicrobials; for example, in water treatment, slime control, paint and wood preservation.

For in vitro use, e.g. for topical application, it will often be convenient to compound the selected product with a pharmaceutically-acceptable carrier such as vegetable or mineral oil or an emollient cream. Similarly, they may be dissolved or dispersed in liquid carriers or solvents, such as water, alcohol, glycols or mixtures thereof or other pharmaceutically-acceptable inert media; that is, media which have no harmful effect on the active ingredient. For such purposes, it will generally be acceptable to employ concentrations of active ingredients of from about 0.01 percent to about 10 percent by weight based on total composition.

Additionally, many compounds of this invention are active versus Gram-positive and certain Gram-negative microorganisms in vivo via the oral and/or parenteral routes of administration in animals, including man. Their in vivo activity is more limited as regards susceptible organisms and is determined by the usual procedure which comprises infecting mice of substantially uniform weight with the test organism and subsequently treating them orally or subcutaneously with the test compound. In practice, the mice, e.g. 10, are given an intraperitoneal inoculation of suitably diluted cultures containing approximately 1 to 10 times the $LD_{100}$ (the lowest concentration of organisms required to produce 100% deaths). Control tests are simultaneously run in which mice receive inoculum of lower dilutions as a check on possible variation in virulence of the test organism. The test compound is administered 0.5 hour post-inoculation, and is repeated 4, 24 and 48 hours later. Surviving mice are held for four days after the last treatment and the number of survivors is noted.

When used in vivo, these novel compounds can be administered orally or parenterally, e.g. by subcutaneous or intramuscular injection, at a dosage of from about 1 mg./kg. to about 200 mg./kg. of body weight per day. The favored dosage range is from about 5 mg./kg. to about 100 mg./kg. of body weight per day and the preferred range from about 5 mg./kg. to about 50 mg./kg. of body weight per day. Vehicles suitable for parenteral injection may be either aqueous such as water, isotonic saline, isotonic dextrose, Ringer's solution, or nonaqueous such as fatty oils of vegetable origin (cotton seed, peanut oil, corn, sesame), dimethylsulfoxide and other non-aqueous vehicles which will not interfere with therapeutic efficiency of the preparation and are non-toxic in the volume or proportion used (glycerol, propylene glycol, sorbitol). Additionally, compositions suitable for extemporaneous preparation of solutions prior to administration may advantageously be made. Such compositions may include liquid diluents; for example, propylene glycol, diethyl carbonate, glycerol, sorbitol, etc.; buffering agents, hyaluronidase, local anesthetics and inorganic salts to afford desirable pharmacological properties. These compounds may also be combined with various pharmaceutically-acceptable inert carriers including solid diluents, aqueous vehicles, non-toxic organic solvents in the form of capsules, tablets, lozenges, troches, dry mixes, suspensions, solutions, elixirs and parenteral solutions or suspensions. In general, the compounds are used in various dosage forms at concentration levels ranging from about 0.5 percent to about 90 percent by weight of the total composition.

In the Examples presented herein, no effort was made to recover the maximum amount of product produced or to optimize the yield of a given product. The Examples are merely illustrative of the process and of the products obtainable thereby. In each of Examples 1, 3 and 5, the principle epimer of Preparation A is used as starting material. In Examples 2 and 4 the starting 4''-deoxy-4''-amino-oleandomycin derivative is a mixture of the 4''-amino epimers.

EXAMPLE 1

11-Acetyl-4''-deoxy-4''-phenylglyoxamido-oleandomycin

A solution of N,N'-dicyclohexylcarbodiimide (2.26 g., 11.0 mmoles) in dry methylene chloride (10 ml.) is added all at once to a solution of 11-acetyl-4''-deoxy-4''-amino-oleandomycin (4.0 g., 5.5 mmoles) and benzoylformic acid (2.47 g., 16.5 mmoles) in dry methylene chloride (40 ml.) at ambient temperature. The reaction mixture is stirred for 24 hours at ambient temperature and is then filtered to remove by-product N,N'-dicyclohexylurea. The filtrate is evaporated to dryness under reduced pressure and the resulting foam is chromatographed on silica gel using acetone as eluting agent. Evaporation of the eluate gives 1.89 g. (40% yield) of the title compound as an amorphous solid.

$^1$H NMR (60 MHz) $\delta_{CDCl_3}^{TMS}$ (ppm): 2.43 (3H, s, acetyl $CH_3$—), 2.33 [6H, s, —$N(CH_3)_2$], 2.71 (2H, m, epoxide), 3.51 (3H, s, —$OCH_3$), aromatic protons: multiplets (5H) in regions 7.19–7.75 (3H) and 8.26–8.49 (2H).

Repetition of the above procedure, but substituting the appropriate reactant $R_3$—C(=O)—C(=O)—OH for benzoylformic acid provides the following compounds:

11-acetyl-4''-deoxy-4''-(2-furyl)glyoxamido-oleandomycin (yield=73%).

$^1$H NMR (60 MHz) $\delta_{CDCl_3}^{TMS}$ (ppm): 2.08 (3H, s, acetyl $CH_3$—), 2.30 [6H, s, —$N(CH_3)_2$], 3.43 (3H, s, —$OCH_3$), 6.64, 7.78, 8.16 (each 1H, m, aromatic protons).

11-acetyl-4''-deoxy-4''-(2-thienyl)glyoxamido-oleandomycin (yield=44%).

$^1$H NMR (60 MHz) $\delta_{CDCl_3}^{TMS}$ (ppm): 2.07 (3H, s, acetyl $CH_3$—), 2.30 [6H, s, —$N(CH_3)_2$], 2.65 (2H, m, epoxide), 3.44 (3H, s, —$OCH_3$), aromatic protons: 7.20 (1H, dd, $J_1$=4Hz, $J_2$=4Hz), 7.82 (1H, d, J=4Hz), 8.42 (1H, d, J=4Hz).

11-acetyl-4''-deoxy-4''-(4-pyridyl)glyoxamido-oleandomycin (yield=55%).

$^1$H NMR (60 MHz) $\delta_{CDCl_3}^{TMS}$ (ppm): 2.04 (3H, s, acetyl $CH_3$—), 2.30 [6H, s, —$N(CH_3)_2$], 3.43 (3H, s, —$OCH_3$), AB pattern with $H_A$ centered at 7.70, $H_B$ at 8.78 ($J_{AB}$=6Hz, 4H, aromatic protons).

11-acetyl-4"-deoxy-4"-(4-methoxyphenyl)glyoxamido-oleandomycin (yield=95%).

$^1$H NMR (60 MHz) $\delta_{CDCl_3}^{TMS}$ (ppm): 2.10 (3H, s, acetyl CH$_3$—), 2.33 [6H, s, —NH(CH$_3$)$_2$], 2.68 (2H, m, epoxide), 3.47 (3H, s, —OCH$_3$ at C-4"), 3.81 (3H, s, —OCH$_3$), AB pattern with H$_A$ centered at 6.97, H$_B$ at 7.41 (J$_{AB}$=9Hz, 4H, aromatic protons).

EXAMPLE 2

Following the procedure of Example 1 but using as reactants the appropriate 11-alkanoyloxy-4"-deoxy-4"-amino-oleandomycin and the appropriate arylglyoxylic acids of formula R$_3$—C(=O)—C(=O)—OH, the compounds tabulated below are produced (Ac=acetyl and Pr=propionyl in the table below).

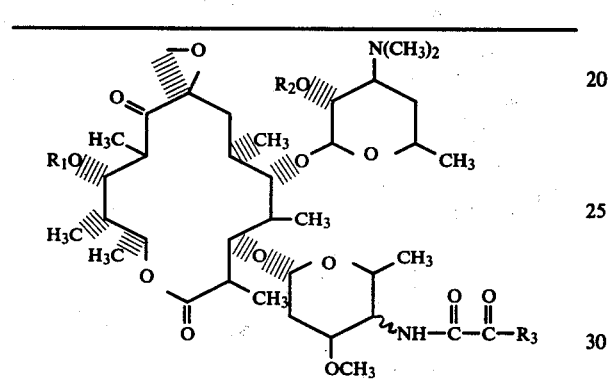

| R$_1$ | R$_2$ | R$_3$ |
|---|---|---|
| Ac | H | 2-ClC$_6$H$_4$ |
| Ac | H | 4-BrC$_6$H$_4$ |
| Pr | H | C$_6$H$_5$ |
| Pr | H | 2-FC$_6$H$_4$ |
| Pr | H | 3-ClC$_6$H$_4$ |
| Ac | Ac | 2-ClC$_6$H$_4$ |
| Ac | Pr | 3-BrC$_6$H$_4$ |
| Ac | Ac | C$_6$H$_5$ |
| Pr | Pr | 3-ClC$_6$H$_4$ |
| Ac | H | 2-(CH$_3$)$_2$NC$_6$H$_4$ |
| Ac | Ac | 4-(CH$_3$)$_2$NC$_6$H$_4$ |
| Pr | H | 2-CH$_3$C$_6$H$_4$ |
| Ac | H | 4-t-C$_4$H$_9$C$_6$H$_4$ |
| Pr | Ac | 4-C$_2$H$_5$C$_6$H$_4$ |
| Ac | H | 2-CH$_3$OC$_6$H$_4$ |
| Ac | H | 2-NO$_2$C$_6$H$_4$ |
| Pr | Pr | 4-NO$_2$C$_6$H$_4$ |
| Ac | H | 4-NO$_2$C$_6$H$_4$ |
| Ac | H | 4-n-C$_4$H$_9$OC$_6$H$_4$ |
| Pr | H | 3-i-C$_3$H$_7$OC$_6$H$_4$ |
| Ac | H | 2,4-Cl$_2$C$_6$H$_3$ |
| Pr | H | 3,5-Cl$_2$C$_6$H$_3$ |
| Ac | H | 2,4-Br$_2$C$_6$H$_3$ |
| Ac | Ac | 4-Cl-2-CH$_3$OC$_6$H$_3$ |
| Ac | H | 3-Cl-6-CH$_3$OC$_6$H$_3$ |
| Pr | H | 2-Br-5-ClC$_6$H$_3$ |
| Ac | H | 3-Cl-5-FC$_6$H$_3$ |
| Ac | H | 4-(CH$_3$)$_2$N-2-C$_2$H$_5$OC$_6$H$_3$ |
| Pr | H | 2-t-C$_4$H$_9$-4-(CH$_3$)$_2$NC$_6$H$_3$ |
| Ac | Ac | 4-Br-2-t-C$_4$H$_9$C$_6$H$_3$ |
| Ac | Ac | 5-Cl-2-C$_2$H$_5$OC$_6$H$_3$ |
| Pr | Pr | 5-Cl-2-C$_2$H$_5$C$_6$H$_3$ |
| Ac | Ac | 2-Cl-4-NO$_2$C$_6$H$_3$ |
| Ac | H | 4-Cl-2-NO$_2$C$_6$H$_3$ |
| Pr | H | 4-Br-3-NO$_2$C$_6$H$_3$ |
| Ac | Ac | 2-t-C$_4$H$_9$-5-NO$_2$C$_6$H$_3$ |
| Ac | H | 2-t-C$_4$H$_9$-5-i-C$_3$H$_7$C$_6$H$_3$ |
| Ac | H | 2,4-(CH$_3$O)$_2$C$_6$H$_3$ |
| Pr | H | 4-CH$_3$O-3-CH$_3$C$_6$H$_3$ |
| Ac | Ac | 4-n-C$_4$H$_9$O-3-CH$_3$OC$_6$H$_3$ |
| Ac | H | 2,4,6-Cl$_3$C$_6$H$_2$ |
| Ac | H | 2-Br-3,6-Cl$_2$C$_6$H$_2$ |
| Pr | H | 2,3-Cl$_2$-6-FC$_6$H$_2$ |

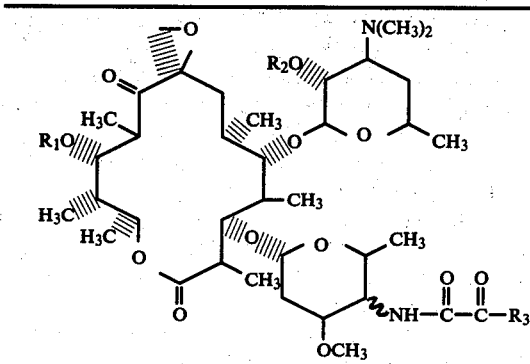

| R$_1$ | R$_2$ | R$_3$ |
|---|---|---|
| Ac | Ac | 4-Br-2,6-(CH$_3$O)$_2$C$_6$H$_2$ |
| Pr | Pr | 4-Br-2,5-(CH$_3$)$_2$C$_6$H$_2$ |
| Ac | H | 4-C$_4$H$_9$O-3,5-Cl$_2$C$_6$H$_2$ |
| Pr | H | 2,6-(CH$_3$)$_2$-4-NO$_2$C$_6$H$_2$ |
| Ac | H | 3,4,5-(OH$_3$O)$_3$C$_6$H$_2$ |
| Ac | Ac | 2,4,6-F$_3$C$_6$H$_2$ |
| Pr | Ac | 4-n-C$_4$H$_9$O-3,5-(CH$_3$O)$_2$C$_6$H$_2$ |
| Ac | Pr | 4,5-(C$_2$H$_5$O)$_2$-2-NO$_2$C$_6$H$_2$ |
| Ac | H | 2,4,6-(t-C$_4$H$_9$)$_3$C$_6$H$_2$ |
| H | Pr | C$_6$H$_5$ |
| H | H | 4-ClC$_6$H$_4$ |
| H | H | 4-CH$_3$OC$_6$H$_4$ |
| H | Ac | 2,6-(CH$_3$O)$_2$C$_6$H$_3$ |
| H | Ac | 6-CH$_3$O-4-CH$_3$C$_6$H$_3$ |
| H | Pr | 5-Cl-2-CH$_3$OC$_6$H$_3$ |
| H | Ac | 4-NO$_2$C$_6$H$_4$ |
| H | Pr | 2-(CH$_3$)$_2$N-C$_6$H$_4$ |
| H | Pr | 2-t-C$_4$H$_9$-4-(CH$_3$)$_2$NC$_6$H$_3$ |
| H | Ac | 2,4,6-Cl$_3$C$_6$H$_2$ |
| H | Ac | 3,4,5-(CH$_3$O)$_3$C$_6$H$_2$ |
| H | H | 2,5-(CH$_3$O)$_2$-4-NO$_2$C$_6$H$_2$ |
| H | H | 2,4,6-(C$_2$H$_5$)$_3$C$_6$H$_2$ |
| Ac | Ac | 2-furyl |
| H | H | 3-furyl |
| H | Pr | 2-furyl |
| H | Ac | 2-thienyl |
| H | H | 3-thienyl |
| Ac | Ac | 2-thienyl |
| Pr | Pr | 4-pyridyl |
| Ac | Ac | 2-pyridyl |
| H | Ac | 3-pyridyl |
| Ac | H | n-C$_3$H$_7$ |
| Ac | Ac | n-C$_4$H$_9$ |
| Ac | Ac | CH$_3$ |
| Ac | H | t-C$_4$H$_9$ |
| Pr | H | CH$_3$ |
| Pr | Pr | sec-C$_4$H$_9$ |
| H | H | 4-pyridyl |
| H | H | 3-pyridyl |
| H | H | 2-pyridyl |
| H | H | n-C$_3$H$_7$ |
| H | H | sec-C$_4$H$_9$ |

EXAMPLE 3

11-Acetyl-4"-deoxy-4"-benzoylthioformamido-oleandomycin

To a solution of 11-acetyl-4"-deoxy-4"-amino-oleandomycin (1.5 g., 2.1 mmoles) and triethylamine (0.29 ml., 2.1 mmoles) in methylene chloride (30 ml.) is added benzoylthioformylchloride (0.38 g., 2.1 mmoles) at 25° C. The reaction mixture is stirred for 15 minutes, at the end of which period an additional 0.25 mole equivalent of each of benzoylthioformyl chloride and triethylamine is added. The stirring and addition of acyl chloride and triethylamine is repeated three more times. The reaction mixture is then diluted with methylene chloride (150 ml.) and water (150 ml.). The pH of the aqueous phase is adjusted to 8.5 with 1 N aqueous sodium hydroxide, the organic layer separated and dried (Na$_2$SO$_4$) and evaporated to dryness under reduced pressure to give 1.9 g. of yellow foam. It is purified by column chromatography on silica gel (4×40 cm. column) using acetone as eluting agent. Evaporation of the eluate affords a quantitative yield of the title product as an amorphous solid.

$^1$H NMR (60 MHz) $\delta_{CDCl_3}^{TMS}$ (ppm): 2.07 (3H, s, acetyl CH$_3$—), 2.32 [6H, s, —NH(CH$_3$)$_2$], 2.68 (2H, m, epoxide), 3.55 (3H, s, —OCH$_3$), 7.30–7.68 (3H, m) and 7.96–8.24 (2H, m, aromatic protons).

In like manner, the following compounds are prepared as amorphous solids by substituting reactant R$_3$—C(=O)—C(=S)—Cl for benzoylthioformyl chloride:

11-acetyl-4''-deoxy-4''-(2-furoyl)thioformamido-oleandomycin (yield=77%).

$^1$H NMR (60 MHz) $\delta_{CDCl_3}^{TMS}$ (ppm): 2.09 (3H, s, acetyl CH$_3$—), 2.34 [6H, s, —NH(CH$_3$)$_2$], 2.69 (2H, m, epoxide), 3.47 (3H, s, —OCH$_3$), aromatic protons: 6.62 (1H, dd, J$_1$=1Hz, J$_2$=4Hz), 7.76 (1H, d, J=1Hz), 8.04 (1H, d, J=4Hz).

11-acetyl-4''-deoxy-4''-(2-thenoyl)thioformamido-oleandomycin (yield=81%).

$^1$H NMR (60 MHz) $\delta_{CDCl_3}^{TMS}$ (ppm): 2.09 (3H, s, acetyl CH$_3$—), 2.33 [6H, s, —NH(CH$_3$)$_2$], 2.69 (2H, m, epoxide), 3.47 (3H, s, —OCH$_3$), aromatic protons: 7.21 (1H, dd, J$_1$=4Hz, J$_2$=4Hz), 7.84 (1H, d, J=4Hz), 8.31 (1H, d, J'4Hz).

11-acetyl-4''-deoxy-4''-(4-methoxybenzoyl)thioformamido-oleandomycin (yield=89%).

$^1$H NMR (60 MHz) $\delta_{CDCl_3}^{TMS}$ (ppm): 2.06 (3H, s, acetyl CH$_3$—), 2.31 [6H, s, —NH(CH$_3$)$_2$], 2.69 (2H, m, epoxide), 3.56 (3H, s, —OCH$_3$ at C-4''), 3.90 (3H, s, —OCH$_3$), AB pattern with H$_A$ centered at 6.95, H$_B$ at 8.15 (J$_{AB}$=9Hz, 4H, aromatic protons).

11-acetyl-4''-deoxy-4''-(4-bromobenzoyl)thioformamido-oleandomycin (yield=20%).

$^1$H NMR (60 MHz) $\delta_{CDCl_3}^{TMS}$ (ppm): 2.05 (3H, s, acetyl CH$_3$—), 2.30 [6H, s, —NH(CH$_3$)$_2$], 2.65 (2H, m, epoxide), 3.50 (3H, s, —OCH$_3$), AB pattern with H$_A$ centered at 7.55, H$_B$ at 7.91 (J$_{AB}$=8Hz, 4H, aromatic protons).

11-acetyl-4''-deoxy-4''-(3,4-dichlorobenzoyl)thioformamido-oleandomycin (yield=60%).

$^1$H NMR (60 MHz) $\delta_{CDCl_3}^{TMS}$ (ppm): 2.10 (3H, s, acetyl CH$_3$—), 2.35 [6H, s, —NH(CH$_3$)$_2$], 2.71 (2H, m, epoxide), 3.55 (3H, s, —OCH$_3$), aromatic protons: 7.53 (1H, d, J=8Hz), 7.95 (1H, dd, J$_1$=8Hz, J$_2$=1Hz), 8.19 (1H, d, J=1Hz).

11-acetyl-4''-deoxy-4''-(4-nitrobenzoyl)thioformamido-oleandomycin (yield=69% crude; i.e. not subjected to column chromatography).

$^1$H NMR (60 MHz) $\delta_{CDCl_3}^{TMS}$ (ppm): 2.06 (3H, s, acetyl CH$_3$—), 2.30 [6H, s, —N(CH$_3$)$_2$], 2.66 (2H, m, epoxide), 3.56 (3H, s, —OCH$_3$), 8.26 (4H, s, aromatic protons).

11-acetyl-4''-deoxy-4''-(2,4,6-trimethylbenzoyl)thioformamido-oleandomycin (yield=93%).

$^1$H NMR (60 MHz) $\delta_{CDCl_3}^{TMS}$ (ppm): 2.13 (3H, s, acetyl CH$_3$—), 2.37 [15H, s, —N(CH$_3$)$_2$ and aryl CH$_3$—], 2.74 (2H, m, epoxide), 3.44 (3H, s, —OCH$_3$), 6.92 (2H, s, aromatic protons).

EXAMPLE 4

The procedure of Example 3 is repeated but using the appropriate 4''-deoxy-4''-amino-oleandomycin and the appropriate R$_3$—C(=O)—C(=S)—Cl reactants to produce the following compounds. (In the table, Ac=acetyl and Pr=propionyl.)

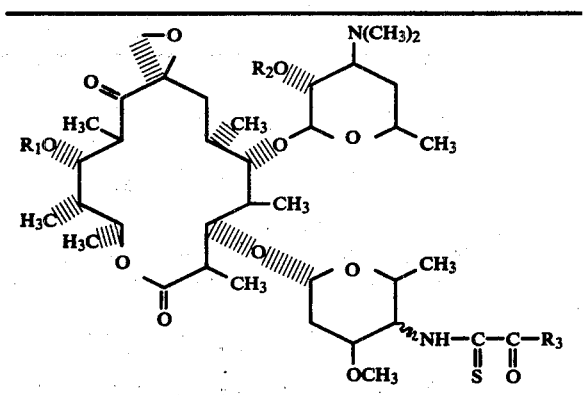

| R$_1$ | R$_2$ | R$_3$ |
|---|---|---|
| Ac | H | 2-ClC$_6$H$_4$ |
| Ac | H | 3-ClC$_6$H$_4$ |
| Ac | H | 4-FC$_6$H$_4$ |
| Pr | H | 2-F-C$_6$H$_4$ |
| Ac | H | 2-CH$_3$C$_6$H$_4$ |
| Ac | Ac | 3-C$_2$H$_5$C$_6$H$_4$ |
| Ac | Pr | 4-t-C$_4$H$_9$C$_6$H$_4$ |
| Ac | H | 2-CH$_3$OC$_6$H$_4$ |
| Pr | Pr | 3-i-C$_3$H$_7$OC$_6$H$_4$ |
| Pr | H | 4-n-C$_4$H$_9$OC$_6$H$_{176}$ |
| Ac | H | 3-(CH$_3$)$_2$NC$_6$H$_4$ |
| Pr | H | C$_6$H$_5$ |
| Pr | Pr | 4-ClC$_6$H$_4$ |
| Pr | Ac | 3-BrC$_6$H$_4$ |
| Pr | Pr | 4-CH$_3$OC$_6$H$_4$ |
| Pr | H | 3-(CH$_3$)$_2$NC$_6$H$_4$ |
| Ac | H | 4-NO$_2$C$_6$H$_4$ |
| Pr | H | 3-NO$_2$C$_6$H$_4$ |
| Ac | Ac | 2-NO$_2$C$_6$H$_4$ |
| Ac | H | 5-Br-2-C$_2$H$_5$OC$_6$H$_3$ |
| Ac | H | 5-Br-2-n-C$_4$H$_9$OC$_6$H$_3$ |
| Pr | H | 5-Cl-2-CH$_3$OC$_6$H$_3$ |
| Ac | H | 2-n-C$_4$H$_9$O-3-CH$_3$C$_6$H$_3$ |
| Pr | H | 2,4-Br$_2$C$_6$H$_3$ |
| Ac | H | 2,5-Cl$_2$C$_6$H$_3$ |
| Ac | Ac | 3-F-4-CH$_3$OC$_6$H$_3$ |
| Pr | Pr | 4-F-2-CH$_3$C$_6$H$_3$ |
| Ac | Pr | 4-F-2-CH$_3$C$_6$H$_3$ |
| Ac | Ac | 2,4-(CH$_3$O)$_2$C$_6$H$_3$ |
| Pr | Pr | 2,6-(CH$_3$O)$_2$C$_6$H$_3$ |
| Pr | Ac | 3-C$_2$H$_5$O-4-CH$_3$OC$_6$H$_3$ |
| Ac | H | 2,3-(CH$_3$)$_2$C$_6$H$_3$ |
| H | H | 2,6-(CH$_3$)$_2$C$_6$H$_3$ |
| H | H | 3,5-(t-C$_4$H$_9$)$_2$C$_6$H$_3$ |
| H | H | 2-C$_2$H$_5$O-3-C$_2$H$_5$C$_6$H$_3$ |
| H | H | C$_6$H$_5$ |
| H | H | 4-ClC$_6$H$_4$ |
| H | H | 2-FC$_6$H$_4$ |
| H | H | 3-CH$_3$C$_6$H$_4$ |
| H | H | 4-t-C$_4$H$_9$C$_6$H$_4$ |
| H | H | 2-CH$_3$OC$_6$H$_4$ |
| H | H | 4-n-C$_4$H$_9$OC$_6$H$_4$ |
| H | H | 4-(CH$_3$)$_2$NC$_6$H$_4$ |
| H | H | 4-NO$_2$C$_6$H$_4$ |
| H | Ac | C$_6$H$_5$ |

-continued

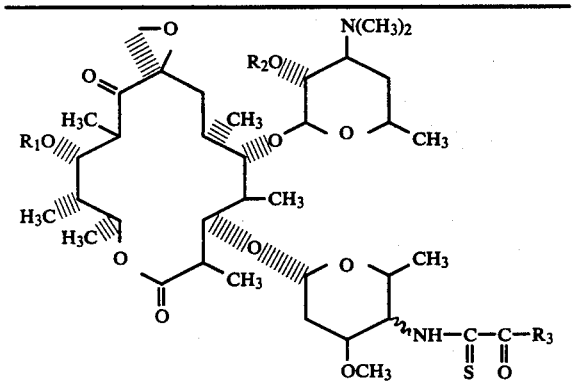

| R₁ | R₂ | R₃ |
|---|---|---|
| H | Br | 3-BrC$_6$H$_4$ |
| H | Ac | 2-NO$_2$C$_6$H$_4$ |
| H | Pr | 2-(CH$_3$)$_2$NC$_6$H$_4$ |
| Ac | H | 2-furyl |
| Pr | H | 3-furyl |
| Ac | H | 2-thienyl |
| Ac | H | 2-pyridyl |
| Pr | H | 3-pyridyl |
| H | H | 4-pyridyl |
| Ac | Ac | 2-pyridyl |
| Pr | Pr | 3-thienyl |
| H | H | 2-pyridyl |
| Ac | H | 3,4,5-(CH$_3$)$_3$C$_6$H$_2$ |
| Ac | H | 2-Cl-4-NO$_2$C$_6$H$_3$ |
| Ac | H | 2,5-Cl$_2$-4-CH$_3$OC$_6$H$_2$ |
| Pr | H | 3,5-Cl$_2$-2-CH$_3$OC$_6$H$_2$ |
| H | H | 2,6-(CH$_3$O)$_2$-4-CH$_3$C$_6$H$_2$ |
| Ac | Ac | 4,5-(CH$_3$O)$_2$-2-CH$_3$C$_6$H$_2$ |
| Ac | H | 2,4-(CH$_3$)$_2$-3-NO$_2$C$_6$H$_2$ |
| Pr | H | 4,5-(CH$_2$)$_2$-2-NO$_2$C$_6$H$_2$ |
| H | H | 3,4,5-Cl$_3$C$_6$H$_2$ |
| Ac | Ac | 2,3,4-Cl$_3$C$_6$H$_2$ |
| Ac | H | 2,4,6-(t-C$_4$H$_9$)$_3$C$_6$H$_2$ |
| Pr | H | 2,4,6-(C$_2$H$_5$)$_3$C$_6$H$_2$ |
| Pr | Pr | 2,4,6-(i-C$_3$H$_7$)$_3$C$_6$H$_2$ |
| Ac | Ac | 2,4,6-(CH$_3$O)$_3$C$_6$H$_2$ |
| H | H | 3,4,5-(CH$_3$O)$_3$C$_6$H$_2$ |
| Ac | Ac | CH$_3$ |
| Ac | H | CH$_3$ |
| Ac | H | i-C$_3$H$_7$ |
| Pr | H | C$_2$H$_5$ |
| Pr | Pr | n-C$_4$H$_9$ |
| Ac | H | t-C$_4$H$_9$ |
| H | H | 3-pyridyl |
| H | H | 2-thienyl |
| H | H | 3-thienyl |
| H | H | 2-furyl |
| H | H | 3-furyl |
| H | H | C$_2$H$_5$ |
| H | H | i-C$_3$H$_7$ |
| H | H | n-C$_4$H$_9$ |

EXAMPLE 5

11-Acetyl-4"-deoxy-4"-(4-aminobenzoyl)thioformamido-oleandomycin

A solution of 11-acetyl-4"-deoxy-4"-(4-nitrobenzoyl)-thioformamido-oleandomycin (830 mg., 0.9 mmole) in ethyl acetate (150 ml.) is hydrogenated in a Parr apparatus at 40 p.s.i. and 25° C. for three hours over 500 mg. of 10% palladium-on-carbon as catalyst. At the end of the three-hour period, an additional 500 mg. of catalyst is added to the reaction mixture and hydrogenation continued for three more hours. The catalyst is then filtered from the reaction mixture and the filtrate evaporated to dryness under reduced pressure. The residue, a foam, is chromatographed on a silica gel column (4×40 cm.) using chloroform/methanol (17/1) for elution. Evaporation of the eluate affords the title compound as a colorless amorphous solid (333 mg., 41% yield).

$^1$H NMR (60 MHz) $\delta_{CDCl_3}^{TMS}$ (ppm): 2.01 (3H, s, acetyl CH$_3$—), 2.32 [6H, s, —N(CH$_3$)$_2$], 3.48 (3H, s, —OCH$_3$), AB pattern with H$_A$ centered at 6.88, H$_B$ at 7.81 (J=8Hz, 4H, aromatic protons).

Following the above procedure, the compounds of Examples 2 and 4 which contain a nitro group in the R$_3$ moiety are reduced to the corresponding amino derivatives.

EXAMPLE 6

The 2'-alkanoyl groups of the compounds of Examples 2 and 4 which contain such a group are removed by subjecting them to solvolysis. The procedure comprises stirring the 2'-alkanoyl containing compound in excess methanol under nitrogen at ambient temperature for about 18 hours. Evaporation of the solvent under reduced pressure affords the corresponding 2'-alcohols.

EXAMPLE 7

11,2'-Diacetyl-4"-deoxy-4"-phenylglyoxamido-oleandomycin (by acetylation of 11-monoacetyl derivative)

Acetic anhydride (0.188 ml., 2.0 mmoles) is added to a solution of 11-monoacetyl-4"-deoxy-4"-phenylglyoxamido-oleandomycin (1.64 g., 2.0 mmoles) in benzene (15 ml.) under a nitrogen atmosphere at room temperature. The mixture is stirred for three hours and is then poured into water (25 ml.) layered with benzene (25 ml.). The pH is adjusted to 9.5 with 6N NaOH and the benzene layer separated. It is washed successively with water and brine and then dried (Na$_2$SO$_4$) and concentrated under reduced pressure to a foam.

Similarly, the 11-monoalkanoyl compounds of Examples 1–4 are converted to their corresponding 11-alkanoyl 2'-acetyl derivatives and, by replacement of acetic anhydride with propionic anhydride, to their corresponding 11-alkanoyl2'-propionyl derivatives.

EXAMPLE 8

4"-Deoxy-4"-Benzoylthioformamido-oleandomcyin

To a 25° C. solution of 2'-acetyl-4"-deoxy-4"-amino-oleandomycin (2.0 g., 2.7 mmoles) and triethylamine (0.38 ml., 2.7 mmoles) in 50 ml. of dry methylene chloride, benzoylthioformyl chloride (0.51 g., 2.7 mmoles) is added. After one hour, additional triethylamine (0.38 ml., 2.7 mmoles) and benzoylthioformyl chloride (0.30 g., 1.6 mmoles) is added to the reaction mixture. Water (150 ml.) and methylene chloride (100 ml.) are then added, and the pH of the aqueous layer adjusted to 9.5 by addition of 1 N aqueous sodium hydroxide. The organic layer is washed with 100 ml. of water, dried over anhydrous sodium sulfate, and rotoevaporated to afford crude 2'-acetyl-4"-deoxy-4"-benzoylthioformamido-oleandomycin as an amber foam (3.0 g.). The crude product is chromatographed on a silica gel column (200 g. silica gel; chloroform/isopropanol=9:1 by volume; column dimensions: 3.5×50 cm.) to afford pure 2'-acetyl-4"-deoxy-4"-benzoylthioformamido-oleandomycin as a colorless foam (1.9 g.; 80% yield).

$^1$H NMR (60 MHz) $\delta_{CDCl_3}^{TMS}$ (ppm):

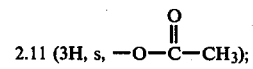

2.11 (3H, s, —O—C(=O)—CH$_3$);

2.31 [6H, s, —N(CH₃)₂]; 3.54 (3H, s, —OCH₃); multiplets at 7.4–7.66 (3H) and 7.95–8.15 (2H), aromatic protons.

Overnight stirring of the 2′-acetyl ester in 50 ml. of anhydrous methanol (25° C.), followed by solvent removal in vacuo, afforded pure 4″-deoxy-4″-benzoylthioformamido-oleandomycin in quantitative yield as a colorless foam.

$^1$H NMR (60 MHz) $\delta_{CDCl_3}^{TMS}$ (ppm): 2.34 [6H, s, —N(CH₃)₂]; 3.51 (3H, s, —OCH₃); multiplets at 7.18–7.58 (3H) and 7.88–8.08 (2H), aromatic protons.

EXAMPLE 9

4″-Deoxy-4″-(2-thienyl)glyoxamido-oleandomycin

To a 25° C. solution of 2′-acetyl-4″-deoxy-4″-amino-oleandomycin (2.0 g., 2.7 mmoles) and 2-thenoylformic acid (1.7 g., 11.0 mmoles) in 50 ml. of anhydrous methylene chloride, N,N′-dicyclohexylcarbodiimide [DCCI, 0.85 g., 4.1 mmoles] is added. The N,N′-dicyclohexylurea by-product is filtered off and, to the filtrate, 150 ml. of water and 100 ml. of methylene chloride are added. The pH of the aqueous phase is adjusted to 9.5 with aqueous 1 N sodium hydroxide. The organic layer is separated, dried over anhydrous sodium sulfate, and roto-evaporated to afford crude 2′-acetyl-4″-deoxy-4″(2-thienyl)glyoxamido-oleandomycin (2.7 g.) as an amber foam. Stirring of the 2.7 g. of crude product in methanol (25° C.) overnight afforded crude 4″-deoxy-4″-(2-thienyl)glyoxamido-oleandomycin, which is purified by silica gel chromatography (200 g. silica gel; column dimensions: 3.5×50 cm.; chloroform/isopropanol=9:1 elution).

Yield: 0.80 g. (36%) $^1$H NMR (60 MHz) $\delta_{CDCl_3}^{TMS}$ (ppm): 2.28 [6H, s, —N(CH₃)₂]; 3.40 (3H, s, —OCH₃); multiplets at 7.16 (1H), 7.78 (1H) and 8.36 (1H), thiophene ring protons.

The following compounds are prepared from appropriate reactants in like manner. They are obtained as colorless foams.

4″-deoxy-4″-phenylglyoxamido-oleandomycin (yield=33%). $^1$H NMR (60 MHz) $\delta_{CDCl_3}^{TMS}$ (ppm): 2.26 [6H, s, —N(CH₃)₂], 3.42 (3H, s, —OCH₃), 7.01–7.61 (3H, m), 8.12–8.36 (2H, m), aromatic protons.

4″-deoxy-4″-2-furylglyoxamido-oleandomycin (yield=50%). $^1$H NMR (60 MHz) $\delta_{CDCl_3}^{TMS}$ (ppm): 2.27 [6H, s, —N(CH₃)₂], 3.40 (3H, s, —OCH₃), multiplets at 6.60 (1H), 7.74 (1H), 8.11 (1H), furan ring protons.

4″-deoxy-4″-methylglyoxamido-oleandomycin (yield=71%). $^1$H NMR (60 MHz) $\delta_{CDCl_3}^{TMS}$ (ppm): 2.25 [6H, s, —N(CH₃)₂]; 2.47 (3H, s, —CO—CO—CH₃), 3.38 (3H, s, —OCH₃).

EXAMPLE 10

Acid Addition Salts

To a solution of 11-acetyl-4″-deoxy-4″-benzylthioformamido-oleandomycin (1.0 mmole) in methanol (50 ml.) is added an equimolar proportion of hydrogen chloride and the reaction mixture stirred at room temperature for one hour. Removal of the solvent by evaporation affords the hydrochloride salt.

In like manner, the above-named compound and the remaining compounds described herein are converted to their hydrochloride, hydrobromide, sulfate, acetate, butyrate, citrate, glycolate, tartrate, stearate, pamoate, fumarate, benzoate and aspartate salts.

When the reactant is an 11,2′-dialkanoyl-4″-deoxy-4″-substituted amino-oleandomycin derivative, isopropanol is used as solvent.

Other acid addition salts are prepared by adding sufficient acid to satisfy each of the basic groups present. In this manner poly-acid addition salts of compounds of this invention are prepared.

PREPARATION A

11-Acetyl-4″-deoxy-4″-amino-oleandomycin

To a suspension of 10% palladium-on-charcoal (10 g.) in methanol (100 ml.) is added ammonium acetate (21.2 g.) and the resulting slurry is treated with a solution of 11-acetyl-4″-deoxy-4″-oxo-oleandomycin (20 g.) in 100 ml. of the same solvent. The suspension is shaken at room temperature in a hydrogen atmosphere at an initial pressure of 50 psi. After 1.5 hours, the catalyst is filtered and the filtrate is added with stirring to a mixture of water (1200 ml.) and chloroform (500 ml.). The pH is adjusted from 6.4 to 4.5 and the organic layer is separated. The aqueous layer, after a further extraction with chloroform (500 ml.), is treated with ethyl acetate (500 ml.) and the pH adjusted to 9.5 with 1 N sodium hydroxide. The ethyl acetate layer is separated and the aqueous layer extracted again with ethyl acetate. The ethyl acetate extracts are combined, dried over sodium sulfate and concentrated to a yellow foam (18.6 g.), which on crystallization from diisopropyl ether, provides 6.85 g. of purified product, m.p. 157.5°–160° C., shown by NMR data and thin layer chromatography (TLC) to be a single epimer at the C-4″ position. The TLC system used is CHCl₃:CH₃OH:NH₄OH (9:2:0.1) on silica gel plates. The developing system vanillin:H₃PO₄:C₂H₅OH (5 g.:50 ml.:100 ml.) is sprayed on the TLC plates heated to about 80°–100° C. The major epimer is less polar than is the minor epimer.

NMR (δ, CDCl₃): 3.41 (3H)s, 2.70 (2H)m, 2.36 (6H)s, and 2.10 (3H)s.

The other epimer, which exists in the crude foam to the extent of 20–25%, is obtained by gradual concentration and filtration of the mother liquors.

In like manner, the following mono-alkanoyl and dialkanoyl esters of 4″-deoxy-4″-amino-oleandomycin (both C-4″ epimers) are prepared from the appropriate mono-alkanoyl and dialkanoyl 4″-deoxy-4″-oxo-oleandomycins. When a 2′-ester is prepared, isopropanol is used as solvent.

11,2′-diacetyl-
2′-acetyl-
2′-propionyl-
11,2′-dipropionyl-
11-propionyl-
11-acetyl-2′-propionyl-
11-propionyl-2′-acetyl-

PREPARATION B

4″-Deoxy-4″-amino-oleandomycin

A solution of 2′-acetyl-4″-deoxy-4″-oxo-oleandomycin (20 g.) in methanol (125 ml.), after stirring at room temperature overnight, is treated with ammonium acetate (21.2 g.). The resulting solution is cooled in an ice bath and treated with sodium cyanoborohydride (1.26 g.). The cooling bath is then removed and the reaction mixture allowed to stir at room temperature for 2 hours. The reaction is poured into water (600 ml.) and diethyl ether (600 ml.) and the pH adjusted from 8.3 to 7.5. The ether layer is separated and the aqueous phase extracted with ethyl acetate. The extracts are set aside and the pH of the aqueous adjusted to 8.25. The diethyl ether and ethyl acetate extracts made at this pH are also set aside, and the pH raised to 9.9. The diethyl ether and ethyl acetate extracts at this pH are combined, washed successively with water (1x) and a saturated brine solution and dried over sodium sulfate. The latter extracts, taken at pH 9.9, are concentrated to a foam and chromatographed on silica gel (160 g.), using chloroform as the loading solvent and initial eluate. After eleven fractions, 12 ml. per fraction are taken, the eluate is changed to 5% methanol-95% chloroform. At fraction 370 the eluate is changed to 10% methanol-90% chloroform and at fraction 440, 15% methanol-85% chloroform is used. Fractions 85-260 are combined and concentrated in vacuo to dryness to provide 2.44 g. of the desired product.

NMR ($\delta$, CDCl$_3$): 5.56 (1H) m, 3.36 (3H) s, 2.9 (2H) m, and 2.26 (6H)s.

What is claimed is:

1. A compound having the formula

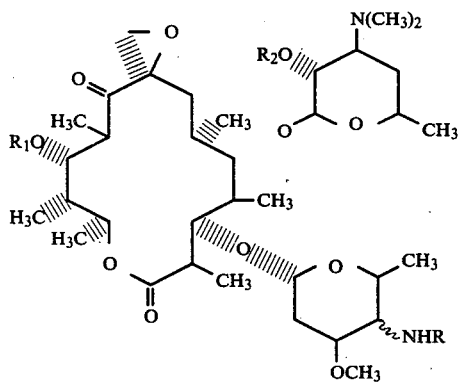

and the pharmaceutically acceptable acid addition salts thereof wherein

R is selected from the group consisting of

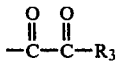 (a)

and

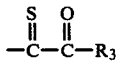 (b)

wherein R$_3$ is selected from the group consisting of a first subgroup consisting of

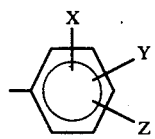

a second subgroup consisting of: heterocyclyl
and a third subgroup consisting of: alkyl having from one to four carbon atoms;
wherein each of X and Y is selected from the group consisting of hydrogen, chloro, bromo, fluoro, alkyl having from one to four carbon atoms and alkoxy having from one to four carbon atoms; and Z is selected from the group consisting of X, dimethylamino, nitro and amino;
heterocyclyl is selected from the group consisting of thienyl, furyl and pyridyl;
and each of R$_1$ and R$_2$ is selected from the group consisting of hydrogen and alkanoyl having from two to three carbon atoms.

2. A compound according to claim 1 wherein R is —C(=O)—C(=O)—R$_3$.

3. A compound according to claim 2 wherein R$_1$ is alkanoyl and R$_2$ is hydrogen.

4. A compound according to claim 2 wherein R$_1$ is acetyl and R$_3$ is

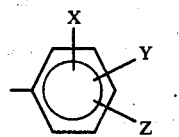

5. A compound according to claim 4 wherein each of X and Y is hydrogen.

6. A compound according to claim 5 wherein Z is chloro.

7. The compound according to claim 5 wherein Z is hydrogen.

8. A compound according to claim 3 wherein R$_1$ is acetyl and R$_3$ is heterocyclyl.

9. A compound according to claim 2 wherein each of R$_1$ and R$_2$ is hydrogen.

10. A compound according to claim 9 wherein R$_3$ is

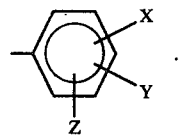

11. A compound according to claim 10 wherein each of X and Y is hydrogen.

12. The compound according to claim 11 wherein Z is hydrogen.

13. A compound according to claim 9 wherein R$_3$ is heterocyclyl.

14. The compound according to claim 13 wherein R$_3$ is 2-thienyl.

15. The compound according to claim 13 wherein R$_3$ is 2-furyl.

16. A compound according to claim 13 wherein R$_3$ is pyridyl.

17. A compound according to claim 1 wherein R is —C(=S)—C(=O)—R$_3$.

18. A compound according to claim 17 wherein R$_1$ is alkanoyl and R$_2$ is hydrogen.

19. A compound according to claim 18 wherein R$_3$ is

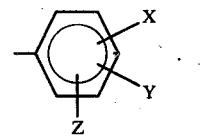

20. A compound according to claim 19 wherein R$_1$ is acetyl, and each of X and Y is hydrogen.

21. The compound according to claim 20 wherein Z is hydrogen.

22. A compound according to claim 18 wherein $R_1$ is acetyl and $R_3$ is heterocyclyl.

23. A compound according to claim 18 wherein $R_1$ is acetyl and $R_3$ is alkyl.

24. A compound according to claim 17 wherein each of $R_1$ and $R_2$ is hydrogen.

25. A compound according to claim 24 wherein $R_3$ is

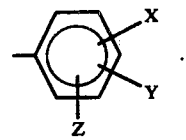

26. A compound according to claim 25 wherein each of X and Y is hydrogen.

27. The compound according to claim 26 wherein Z is hydrogen.

28. A compound according to claim 24 wherein $R_3$ is heterocyclyl.

29. The compound according to claim 28 wherein $R_3$ is 2-furyl.

30. The compound according to claim 28 wherein $R_3$ is 2-thienyl.

31. A compound according to claim 28 wherein $R_3$ is pyridyl.

32. A compound according to claim 24 wherein $R_3$ is alkyl.

* * * * *